United States Patent

Tashiro et al.

Patent Number: 5,374,421
Date of Patent: Dec. 20, 1994

[54] COMPOSITION FOR HAIR TREATMENT

[75] Inventors: Kazuhiro Tashiro, Chiba; Kazuyuki Yahagi, Tokyo, both of Japan

[73] Assignee: Kao Corporation, Tokyo, Japan

[21] Appl. No.: 978,192

[22] Filed: Nov. 18, 1992

Related U.S. Application Data

[63] Continuation of Ser. No. 748,776, Aug. 22, 1991, abandoned.

Foreign Application Priority Data

Aug. 24, 1990 [JP] Japan .................................. 2-224113

[51] Int. Cl.$^5$ .............................................. A61K 7/09
[52] U.S. Cl. .................................................. 424/70.12
[58] Field of Search ..................... 424/70, 71; 514/772

[56] References Cited

U.S. PATENT DOCUMENTS

| | | | |
|---|---|---|---|
| 4,423,041 | 12/1983 | Clum et al. | 514/772 |
| 4,658,839 | 4/1987 | Dallal et al. | 424/70 |
| 4,711,776 | 12/1987 | Suzuki et al. | 424/70 |

*Primary Examiner*—Thurman K. Page
*Assistant Examiner*—William E. Benston, Jr.
*Attorney, Agent, or Firm*—McAulay Fisher Nissen Goldberg & Kiel

[57] ABSTRACT

A composition for hair treatment such as hair rinse, shampoo, or hair conditioner, contains (a) 0.1–10 wt. % of a modified silicone polymer having at least one alkoxy group in the molecule and a melting point of not lower than 30° C., (b) 0.1–20 wt. % of a cationic surface active agent, (c) 0.1–30 wt. % of an oily or fatty material, (d) 0.1–90 wt. % of an organic liquid which is compatible with water and of which molecule has at least one hydroxy group, and (e) water.

7 Claims, No Drawings

COMPOSITION FOR HAIR TREATMENT

This is a continuation of application Ser. No. 07/748,776 filed Aug. 22, 1991 now abandoned.

BACKGROUND OF INVENTION

1. Field of Invention

The present invention relates to a composition for hair treatment. Particularly, the invention relates to a hair treating composition having improved conditioning ability (that is, ability to give certain preferable properties such as smoothness and flexibility to hair).

2. Description of Prior Art

Hair treating compositions not only giving smoothness, flexibility and antistatic property to hair but also dressing hair softly, lightly and gently have been used as hair-rinses, hair-conditioners, hair-creams, styling lotions and other cosmetics for hair treatment.

Heretofore, there has been known a hair treating composition comprising a cationic surface active agent, oily or fatty materials (e.g., higher alcohols, glycerides, liquid paraffin or esters) and an aqueous liquid (e.g., water or a mixture of water and alcohol).

Further, there has been also known a hair treating composition obtained by adding dimethylsiloxane polymer (silicone oil) to the above-mentioned hair treating composition as the oil component or other additional components. Since dimethylsiloxane polymer gives excellent smoothness and gloss to hair, it has been used for many hair treating compositions. However, such hair treating compositions have a drawback that a hair treated with them feels oily and sticky (i.e., they make hair oily, sticky or fatty). Further, there is another drawback that a composition including silicone oil has low dispersion stability preservation stability), because silicone oil generally has poor compatibility with aqueous components such as water and others. In addition to the above-stated drawbacks, the hair treated with the above composition cannot be combed smoothly when it is wet, and the hair does not feel gentle when it is dry.

In order to obviate the above drawbacks, there have been proposed various hair treating compositions containing modified silicones.

In Japanese Patent Publication No. 48(1973)-19941, there is disclosed a hair treating composition containing, as a base material or an additive, an alkoxy-modified silicone having a hydroxyl or a polyoxyalkylene group in the side chain. Since this modified silicone has good compatibility with aqueous components, preservation stability of the composition is improved. However, the hair treating composition using the silicone has poor ability to nave sufficient moisture preserved in hair (so-called "moisture-preservability") because the compound has hydroxyl group in the molecule. Therefore, the hair treated with the composition does not feel gentle when it is dry. Further, the treating composition gives insufficient antistatic effect to the hair.

In Japanese Patent Provisional Publication No. 56(1981)-92808, there is disclosed a hair treating composition containing a quaternary ammonium salt, a higher alcohol and hydrophobic silicone of 1-1,000 cs as main components. As an example of said hydrophobic silicone, aliphatic alcohol-modified polysiloxane is disclosed in the publication. By introducing the aliphatic alcohol-modified polysiloxane, the hair treated with the above-mentionedarticle exhibits improved smoothness when it is dry. But, the hair treating composition can not satisfactorily obviate the drawbacks that the hair cannot be combed smoothly when it is wet and that the wet hair feels sticky, because the above-mentioned polymer is an oily material.

In order to prevent hair from becoming dirty again, there is proposed a hair-conditioning composition containing a silicone conditioning agent (e.g., non-substituted, or amino- or alkoxy-substituted linear polydimethylsiloxanes), dimethicone co-polyol, a lipid vehicle substance, a cationic surface active vehicle substance and water in Japanese Patent Provisional Publication No. 61(1986)-6.

SUMMARY OF THE INVENTION

According to the study of the present inventors, a hair-conditioning rinse using the above composition can obviate sticky feeling of hair because the dimethicone copolyol remarkably suppresses adhesion of vehicle substance, such as a cationic surface active agent, to hair. However, since the amount of vehicle substance adhered to hair is too small, the hair treated with such treating composition has insufficient gentle feeling, poor flexibility and unsatisfactory antistatic property after the composition is rinsed away from the hair.

The object of the present invention is to provide a hair treating composition having excellent conditioning ability which is free from the above-mentioned drawbacks. According to the study of the present inventors, it has been discovered that the above object can be attained by preparing a composition containing, as indispensable components, a specific solid modified silicone polymer, a cationic surface active agent, an oily or fatty material (oil or fat), an organic liquid which is compatible with water and of which molecule has at least one hydroxyl group, and water.

There is provided by the invention a composition for hair treatment containing:

(a) 0.1–10 wt. % of a modified silicone polymer having at least one alkoxy group in the molecule and a melting point of not lower than 30° C., (b) 0.1–20 wt. % of a cationic surface active agent, (c) 0.1–30 wt. % of an oily or fatty material, (d) 0.1–90 wt. % of an organic liquid which is compatible with water and of which molecule has at least one hydroxyl group, and (e) water.

DETAILED DESCRIPTION OF THE INVENTION

The modified silicone polymer employed for the invention (a) is a polymer of which molecule has at least one alkoxy group and of which melting point is not lower than 30° C [namely, it is solid at room temperature (25° C.)]. The molecule may be a linear polymer, a branched polymer or a network polymer. The organosiloxane unit forming the modified silicone polymer may have an alkyl group such as methyl, ethyl and propyl; an alkenyl group such as vinyl and allyl; an aryl group such as phenyl and naphthyl; and a cycloalkyl group such as cyclohexyl; in addition to an alkoxy group. The unit having methyl group is generally employed.

A typical example of the alkoxy group contained in the above-described modified silicone is the group expressed by the following formula (I):

$$-(CH_2)_k O - R^1 \qquad (I).$$

[In the above formula, $R^1$ represents an alkyl group having 1-28 carbon atoms (preferably, 12-22 carbon atoms) and k is an integer of 0-6.]

Typical examples of the alkoxy modified silicone polymer include the polymers expressed by the following formula (II):

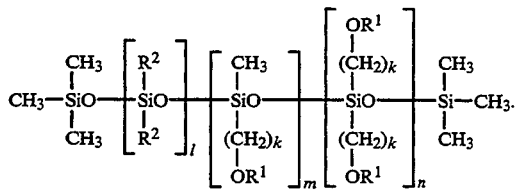
(II)

[In the above formula, $R^2$ represents methyl or phenyl, l is an integer of 1-3,000, m and n are integers satisfying the condition of m+n=1-500, and each of $R^1$ and k is the same as defined in the above formula (I).]

The above-mentioned alkoxy-modified silicone generally has a melting point (m.p.) in the range of 30°-60° C. (preferably 40°-50° C.).

Among the alkoxyl modified silicone polymers expressed by the above formula, a preferable polymer is expressed by the following formula (III):

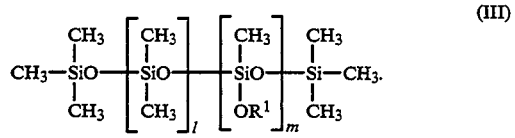
(III)

[In the above formula, l is an integer of 1-100, m is an integer of 1-50 and $R^1$ is the same as defined in the above formula (I).]

Preferred examples of the alkoxy-modified silicone of the formula (III) include stearoxy-modified silicone, cetyloxy-modified silicone and myristyloxy-modified silicone. These modified silicone preferably have "l" of 5-30 (more preferably 6-13), "m" of 2-15 (more preferably 2-9), and m.p. of 40°-50° C.

Since the above-described component (a) has excellent compatibility with oily or fatty material such as higher alcohols, an emulsion containing the component has improved preservation stability. Further, hair treating compositions containing the component (a) has excellent moisture-preservability and a hair treated with the composition does not feel sticky, because the component is a solid substance.

The amount of the modified silicone polymer of the component (a) used for the hair treating composition of the invention generally is within a range of 0.1-10 wt. %, preferably is 0.2-5 wt. %.

Examples of the cationic surface active agent of the component (b) employed for the hair treating composition of the invention include quaternary ammonium salts expressed by the following formula (IV):

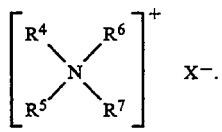
(IV)

[In the above formula, one of $R^4$-$R^7$ or each of two of $R^4$-$R^7$ represents a linear or branched alkyl group having 8-28 carbon atoms, a hydroxyalkyl group having 8-28 carbon atoms or a group expressed by the formula of:

$$R^8-(CH_2CH_2O)_r-$$

(wherein $R^8$ is an alkyl group having 8-24 carbon atoms or a hydroxyalkyl group having 8-28 carbon atoms, and r is an integer of 1-10); the rest of them is benzyl, an alkyl group having 1-3 carbon atom or a hydroxyalkyl group having 1-3 carbon atom; and $X^-$ is halogen ion or an organic anion.]

Among the quaternary ammonium salts expressed by the above formula, particularly preferable are branched quaternary ammonium salts expressed by the following formulae (V) and (VI) which are described in Japanese Patent Provisional Publication No. 61(1986) -267505:

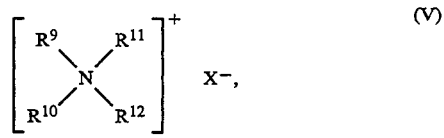
(V)

[In the above formula, each of $R^9$ and $R^{10}$ is an alkyl group selected from the group consisting of a branched alkyl group expressed by the following formula (S):

(S)

and the linear alkyl groups expressed by the following formula (T):

$$CH_3(CH_2)_q- \quad (T).$$

(In the above formulae (S) and (T), $R^{13}$ is methyl or ethyl; each of p and q is an integer satisfying the condition that the total number of carbon atoms is within a range of 8-16 in the formulae (S) and (T), respectively); branching coefficient of $R^9$ and $R^{10}$ [(S)/(S)+(T)] is within a range of 10-100 wt. % (in other words, the branched alkyl group (S) is preferably contained in the formula); each of $R^{11}$ and $R^{12}$ is a group selected from the group consisting of an alkyl group having 1-3 carbon atom(s) and a hydroxyalkyl group having 1-3 carbon atom(s); and $X^-$ is halogen ion or an organic anion.]

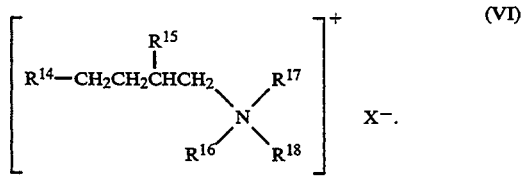
(VI)

[In the above formula, each of $R^{14}$ and $R^{15}$ is an alkyl group having 2-12 carbon atoms; $R^{16}$ is a group expressed by the formula:

(wherein each of $R^{14}$ and $R^{15}$ is the same as defined above), or an alkyl group having 1-3 carbon atom; each of $R^{17}$ and $R^{18}$ is benzyl, an alkyl group having 1-3 carbon atom or a hydroxyalkyl group having 1-3 carbon atom; and $X^-$ is a halogen ion or an organic anion.]

There can be used for the present invention either a single compound or a combination of two or more compounds of the cationic surface active agents expressed by the above formulae.

The amount of the cationic surface active agent of the component (b) contained in the composition of the invention generally is within the range of 0.1-20 wt. %, preferably is within the range of 0.5-5 wt. %.

The oily or fatty material (oil or fat) of the component (c) of the hair treating composition of the invention is not particularly restricted, so far as it is generally employed for a hair treating composition. Examples of the oily or fatty material employed in the invention include higher alcohols having an alkyl group or an alkenyl group of linear chain or branched chain; hydrocarbons such as liquid paraffin, vaseline and solid paraffin; lanolin derivatives such as liquid lanolin and lanolin fatty acid; silicones such as dimethylpolysiloxane; fats such as higher alcohols, higher fatty acid esters and higher fatty acids; linear amido amines having an alkyl group or an alkenyl group; animal or plant fats and oils such as mink oil and olive oil.

In the case where the composition is used as hair-rinse or hair-conditioner, particularly preferred are a mono-glyceride derived from a saturated or unsaturated fatty acid of linear chain or branched chain having 12-24 carbon atoms and a higher alcohol having an alkyl group or an alkenyl group of linear chain or branched chain of 12-26 carbon atoms. Concrete examples of the above preferable oily or fatty materials include fatty acid mono-glyceryl esters such as oleic acid mono-glyceryl ester, palmitic acid mono-glyceryl ester, stearic acid mono-glyceryl ester, behenic acid mono-glyceryl ester and isostearic acid monoglyceryl ester; and higher alcohols such as cetyl alcohol, stearyl alcohol, arachidic alcohol, behenic alcohol, carnaubal alcohol and ceryl alcohol.

The amount of the oily or fatty material of the component (c) contained in the composition of the invention generally is within the range of 0.1-30 wt. %, preferably is within the range of 1.0-10 wt. %.

The component (d) of the hair treating composition of the invention is an organic liquid which is compatible with water and of which molecule has at least one hydroxyl group. Concrete examples of the organic liquids include alcohols such as lower monohydric alcohols (in which the number of carbon atoms is not more than six) [e.g., ethanol, propanol and butanol], polyhydric alcohols [e.g., ethylene glycol, propylene glycol, 1,3-butylene glycol isoprene glycol and glycerol] and polymers of polyhydric alcohol [e.g., diethylene glycol, dipropylene glycol, diglycerol and polyethylene glycol]; alkyl polyalkylene glycol ethers such as alkyl monoethers of diethylene glycol [e.g., diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether and diethylene glycol mono-t-butyl ether] and alkyl monoethers of dipropylene glycol [e.g., dipropylene glycol monomethyl ether, dipropylene glycol monoethyl ether, dipropylene glycol monopropyl ether, dipropylene glycol monobutyl ether, dipropylene glycol monoisopropyl ether and dipropylene glycol mono-t-butyl ether]. Among the above-described substances, polyhydric alcohols and alkyl monoethers of diethylene glycol are particularly preferred for the component (d).

The above-mentioned component (d) permeates hair and preserves moisture in the hair, therefore the component gives to the hair excellent conditioning effects (namely, the hair treated with the composition containing the component feels gentle and has excellent flexibility even if the hair becomes dry).

The amount of the component (d) contained in the hair treating material of the invention generally is within the range of 0.1-90 wt. %, preferably is within the range of 3-50 wt. %.

The component (e) of the hair treating composition of the invention is water. Water is a medium in which the other components are dispersed and emulsified. The amount of water employed is appropriately determined according to the amounts of the other components constituting the composition.

The hair treating composition of the invention may optionally include other components which are generally contained in cosmetics, medicines and foods, so far as they do not disturb the effect of the invention. Examples of the optional components include medicinal chemicals such as dandruff-inhibiting agents, disinfectants and vitamins; antiseptics such as paraben; viscosity increasing agents such as perfluoro-polyethers and water soluble polymers; coloring agents such as dyes and pigments; conditioning agents such as cationic polymers; pearling agents such as glycol esters; polymers for hair-dressing such as acrylic resin liquid; various blended perfumes; and other components described in ENCYCLOPEDIA OF CONDITIONING RINSE INGREDIENTS (MICELLE PRESS 1987).

The hair treating composition of the invention can be prepared in the conventional manner, and can be used as, for example, hair-rinse, hair-conditioner, hair-cream, styling lotion, styling mousse, conditioning mousse, hair spray and other cosmetics for hair-treatment.

The hair treated with the hair treating composition of the invention does not feel oily and sticky, and has excellent smoothness and flexibility, whether it is dry or wet. Further, the hair treating composition of the invention dresses hair softly, lightly and gently, and gives satisfactory antistatic effect to the hair. Therefore, the hair treated with the composition of the invention seems neat and unaffected. In addition to these advantages, the hair treating composition of the invention has good preservation stability.

The following examples further illustrate the present invention, but these examples are by no means understood to restrict the invention.

EXAMPLE 1

A hair treating composition of the invention (a composition for hair-rinse; Sample 1) was prepared in the following manner. The amount of each component is set forth in Table 1.

Stearoxyl modified silicone melted and heated at 70° C., stearoyltrimethylammonium chloride, cetyl alcohol and propylene glycol were added into hot water of 70° C., and then the resulting mixture was stirred to be emulsified. The resulting emulsion was allowed to stand under stirring to reach room temperature. The obtained emulsion was the composition for hair-rinse (Sample 1).

Stearoxyl modified silicone in the above description is the compound illustrated below:

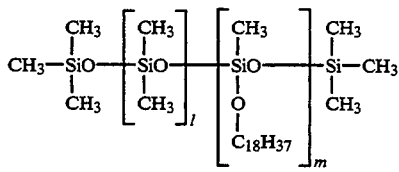

[l = 7–13, m = 2–8, m.p. 40–50° C.]

COMPARISON EXAMPLE 1

The procedures of Example 1 were repeated except for not using propylene glycol, to prepare a hair treating composition (composition for hair-rinse; Comparison Sample 1).

COMPARISON EXAMPLE 2

The procedures of Example 1 were repeated except for using dimethylpolysiloxane instead of stearoxyl modified silicone, to prepare a hair treating composition (composition for hair-rinse; Comparison Sample 2).

Each of the compositions for hair-rinse obtained in the above Example and Comparison Examples was evaluated with respect to the conditioning ability as hair-rinse according to the following tests. The results are set forth in Table 1. The procedures of the tests and evaluations are as follows.

(1) Sensory evaluation of dried hair, with respect to flexibility, smoothness, oily feeling and gentle feeling:

2 g of the sample composition was uniformly applied onto 20 g of a bundle of Japanese women's hair (length: 15 cm) having not been subjected to cosmetic treatments such as cold permanent wave treatment and bleaching treatment, and then rinsed away with flowing water for 30 seconds. The resulting bundle of hair was dried with only a towel (hereinafter, this procedure is referred to as "towel-dry"), and then further dried with a drier.

The obtained bundle of hair was evaluated and classified into following four grades, with respect to each of flexibility, smoothness, oily feeling and gentle feeling.

A: Excellent
B: Good
C: Slightly poor
D: Poor (2) Combing strain:

Wet hair: The bundle of hair treated in the same manner as described in the above (1) was towel-dried, and successively the combing strain of the resulting wet bundle of hair (containing about 0.7 g of water per 1 g of hair was measured by means of a strain gauge.

Dried hair: the bundle of hair treated in the same manner as described in the above (1) was towel-dried, and then further dried with a drier. The combing strain of the resulting bundle of hair was measured by means of a strain gauge.

The measurement was carried out in the air-conditioned room (temperature: 20° C.; relative humidity: 65%), and was repeated for 20 times. The obtained values were averaged to obtain the combing strain (g).

(3) Moisture-preservability:

The bundle of hair treated in the same manner as described in the above (1) was dried with a drier, and then the bundle was left in the air-conditioned room (temperature: 25° C.; relative humidity: 40%) for 24 hours. After 0.3 g of the hair was collected from the resulting bundle, the collected hair was blown by hot nitrogen gas to evaporate the moisture contained in the hair. Then, the amount of the moisture remaining in the hair was measured for 5 times in accordance with Karl-Fischer's method. The obtained values were averaged, and the ratio of the average value to the weight of the hair was calculated to obtain the moisture-preservability (%).

TABLE 1

| compositions (wt. %) | Com.Sam.1 | Com.Sam.2 | Sample 1 |
| --- | --- | --- | --- |
| stearoxyl modified silicone | 2.0 | — | 2.0 |
| dimethylpolysiloxane (1,000 cs) | — | 2.0 | — |
| stearyltrimethylammonium chloride | 2.0 | 2.0 | 2.0 |
| cetyl alcohol | 3.0 | 3.0 | 3.0 |
| propylene glycol | — | 5.0 | 5.0 |
| water | balance | balance | balance |
| total | 100 | 100 | 100 |
| Effect to Hair combing strain (g) | | | |
| wet | 213 | 242 | 192 |
| dry | 82 | 78 | 63 |
| moisture-preservability (%) | 12.3 | 11.8 | 14.0 |
| sense evaluation (dry hair) | | | |
| flexibility | C | B | A |
| smoothness | B | B | A |
| non-oily feeling | B | D | A |
| gentle feeling | C | C | A |

EXAMPLE 2

A hair treating composition of the invention (a composition for hair-rinse; Sample 2) was prepared in the following manner. The amount of each component is set forth in Table 2. The stearoxy-modified silicone used below was the same as that used in Example 1.

At a temperature of 70° C., a mixture consisting of stearoxyl modified silicone (melted at 70° C.), dialkyl-dimethylammonium chloride, cetostearyltrimethylammonium chloride, cetostearyl alcohol, polyoxyethylene cetyl ether, liquid paraffin and propylene glycol was added to a mixture consisting of hydroxyethyl cellulose, antiseptics, dyes and water. After stirring to give an emulsion, the obtained emulsion was further stirred to cool down to 45° C., and then perfumes were added to the emulsion. The resulting mixture was stirred to cool down to room temperature. The obtained emulsion was a composition for hair-rinse (Sample 2).

EXAMPLES 3–7

The procedures of Example 2 were repeated except that the components and their amounts are changed as shown in Table 2, to prepare hair treating compositions of the invention (compositions for hair-rinse; Samples 3–7).

Each of the compositions for hair-rinse obtained in the above examples exhibited excellent conditioning ability.

Cetyloxyl modified silicone and myristyloxyl modified silicone in Table 2 are the compounds expressed by the following formulae.

Cetyloxyl modified silicone:

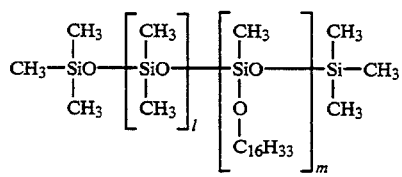

[ l = 7–13, m = 2–8, m.p. 40–50° C.]

Myristyloxyl modified silicone:

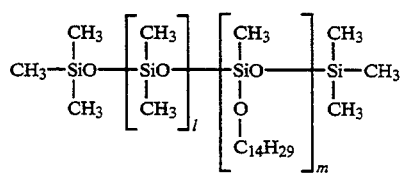

[ l = 6–10, m = 3–9, m.p. 40–50° C.]

TABLE 2

| compositions (wt. %) | Sam.3 | Sam.4 | Sam.5 | Sam.6 | Sam.7 | Sam.8 |
|---|---|---|---|---|---|---|
| stearoxyl modified silicone | 2.0 | — | — | 1.0 | — | — |
| cetyloxyl modified silicone | — | 3.0 | — | — | 1.0 | — |
| myristyloxyl modified silicone | — | — | 1.0 | — | — | 1.0 |
| dialkyldimethyl-ammonium chloride | 1.0 | 0.5 | — | 2.0 | — | 0.5 |
| 2-dodecylhexadecyltri-methyl ammonium chloride | — | — | 1.0 | — | 2.0 | 0.5 |
| cetostearyltrimethyl-ammonium chloride | 1.0 | 1.5 | 1.0 | 1.0 | 1.0 | 1.0 |
| cetostearyl alcohol | 3.0 | 2.5 | 3.0 | 3.0 | 3.0 | 2.5 |
| polyoxyethylene cetyl ether (EO = 5) | 0.2 | 0.2 | 0.2 | 0.3 | 0.3 | 0.3 |
| liquid paraffin | 0.5 | 0.5 | 0.5 | 0.5 | 0.5 | 0.5 |
| propylene glycol | 3.0 | 3.0 | 3.0 | — | — | — |
| diethylene glycol monoethyl ether | — | — | — | 3.0 | 3.0 | 3.0 |
| hydroxyethyl cellulose | 0.3 | 0.3 | 0.3 | — | — | 0.5 |
| hydroxypropylmethyl cellulose | — | — | — | 0.2 | 0.2 | — |
| antiseptics | | | proper quantity | | | |
| dyes | | | very small quantity | | | |
| perfumes | | | very small quantity | | | |
| water | | | balance | | | |
| total | 100 | 100 | 100 | 100 | 100 | 100 |

EXAMPLE 8

A hair treating composition of the invention (composition for hair treatment; Sample 8) was prepared in the following manner. The amount of each component is set forth in Table 3. The stearoxy-modified silicone used below was the same as that used in Example 1.

Glycerol, hydroxyethyl cellulose (1% aqueous solution; viscosity: 8,000 cs) and methylparaben were homogeneously dispersed in water, and then heated. To the resulting dispersion, added and emulsified under stirring was a homogeneous dispersion of heated stearoxyl modified silicone, 2-dodecylhexadecyltrimethylammonium chloride, stearyl-trimethylammonium chloride, cetostearyl alcohol, lanolin, liquid paraffin and polyoxyethlene oleyl ether (EO=5). After cooling, perfumes were added to the resulting emulsion to obtain a composition for hair treatment (Sample 8).

The composition for hair treatment obtained above gave smoothness and excellent flexibility to hair, and the hair treated with the composition felt little oily feeling but good feeling.

TABLE 3

| compositions | (wt. %) |
|---|---|
| stearoxyl modified silicone | 3.0 |
| 2-dodecylhexadecyltrimethyl-ammonium chloride | 1.5 |
| stearyltrimethylammonium chloride | 1.0 |
| cetostearyl alcohol | 3.0 |
| lanolin | 3.0 |
| liquid paraffin | 3.0 |
| glycerol | 5.0 |
| hydroxyethyl cellulose (1% aqueous solution; viscosity: 8,000 cs) | 0.5 |
| polyoxyethlene oleyl ether (EO = 5) | 0.5 |
| methylparaben | 0.2 |
| perfumes | 0.4 |
| water | balance |
| total | 100 |

EXAMPLE 9

A hair treating composition of the invention (composition for hair-cream; Sample 9) was prepared in the following manner. The amount of each component is set forth in Table 4. The stearoxy-modified silicone used below was the same as that used in Example 1.

To hot water, added and emulsified was a homogeneous dispersion of heated dipropylene glycol, glycerol, stearoxyl modified silicone, di-2-hexyldecyldimethylammonium chloride, cetyltrimethylammonium chloride, cetyl alcohol, liquid paraffin and monostearlic polyoxyethylene bitan (EO=20). After the resulting emulsion was stirred to cool down, perfumes were added to obtain a composition for hair-cream (Sample 9).

The composition for hair treatment obtained above gave smoothness and excellent flexibility to hair, and the hair treated with the composition felt little oily feeling but good feeling.

TABLE 4

| compositions | (wt. %) |
|---|---|
| stearoxyl modified silicone | 3.0 |
| di-2-hexyldecyldimethyl-ammonium chloride | 2.0 |
| cetyltrimethylammonium chloride | 1.0 |
| monostearlic polyoxy-ethylene sorbitan (EO = 20) | 0.5 |
| cetyl alcohol | 4.0 |
| liquid paraffin | 2.0 |
| dipropylene glycol | 6.0 |
| glycerol | 10.0 |
| perfumes | 0.4 |
| water | balance |
| total | 100 |

We claim:

1. A composition for hair treatment comprising:
   (a) 0.1–10 wt. % of a silicone polymer having at least one alkoxy group containing 12 to 22 carbon atoms in the molecule and having a melting point of not lower than 30° C.;
   (b) 0.1–20 wt. % of a cationic surface active agent;
   (c) 0.1–30 wt. % of an alcohol having an alkyl group or alkenyl group of 12 to 26 carbon atoms;
   (d) 0.1–90 wt. % of an organic liquid compatible with water which is selected from the group consisting of propylene glycol, alkyl monoethers of diethylene glycol, and alkyl monoethers of dipropylene glycol, and
   (e) water.

2. The composition for hair treatment as defined in claim 1, wherein the modified silicone polymer has the following formula:

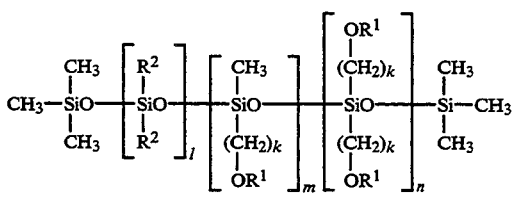
(II)

wherein $R^1$ represents an alkyl group having 1–28 carbon atoms, $R^2$ represents methyl or phenyl, k is an integer of 0–6, l is an integer of 1–3,000, and m and n are integers satisfying the condition of m+n=1–500.

3. The composition for hair treatment as defined in claim 1, wherein the modified silicone polymer has the following formula:

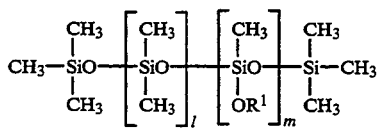

wherein $R^1$ represents an alkyl group having 1–28 carbon atoms, l is an integer of 1–100, and m is an integer of 1–50.

4. The composition for hair treatment as defined in claim 1, wherein the cationic surface active agent has the following formula:

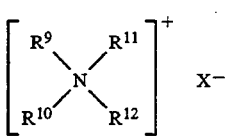

wherein each of $R^9$ and $R^{10}$ is an alkyl group selected from the group consisting of branched alkyl groups expressed by the following formulae:

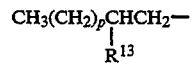

wherein $R^{13}$ is methyl or ethyl; p is an integer satisfying the condition that the total number of carbon atoms is within the range of 8–16;
and the linear alkyl groups expressed by the following formula:

wherein q is an integer satisfying the condition that the total number of carbon atoms is within the range of 8–16; and
each of $R^{11}$ and $R^{12}$ is a group selected from the group consisting of an alkyl group having 1–3 carbon atoms and a hydroxyalkyl group having 1–3 carbon atom; and $X^-$ is a halogen ion or an organic anion.

5. The composition for hair treatment as defined in claim 1, wherein the cationic surface active agent has the following formula:

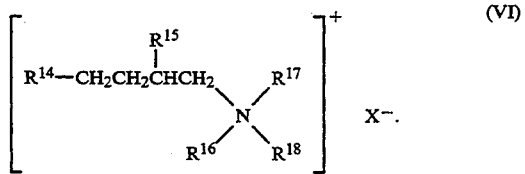
(VI)

wherein each of $R^{14}$ and $R^{15}$ is an alkyl group having 2–12 carbon atoms; $R^{16}$ is the group expressed by the formula:

wherein each of $R^{14}$ and $R^{15}$ is the same as defined above, or an alkyl group having 1–3 carbon atom; each of $R^{17}$ and $R^{18}$ is benzyl group, an alkyl group having 1–3 carbon atom or a hydroxyalkyl group having 1–3 carbon atom; and $X^-$ is halogen ion or an organic anion.

6. The composition for hair treatment as defined in claim 1, wherein the modified silicone polymer is contained in a amount of 0.2–5 wt. %.

7. A method for treating hair comprising applying to the hair a hair treating effective amount of a composition comprising:
   (a) 0.1–10 wt. % of a silicone polymer having at least one alkoxy group containing 12 to 22 carbon atoms in the molecule and having a melting point of not lower than 30° C.:
   (b) 0.1–20 wt. % of a cationic surface active agent;
   (c) 0.1–30 wt. % of an alcohol having an alkyl group or alkenyl group of 12 to 26 carbon atoms;
   (d) 0.1–90 wt. % of an organic liquid compatible with water which is selected from the group consisting of propylene glycol, alkyl monoethers of diethylene glycol, and alkyl monoethers of dipropylene glycol, and
   (e) water.

* * * * *